(12) United States Patent
Gupta et al.

(10) Patent No.: US 10,750,959 B2
(45) Date of Patent: Aug. 25, 2020

(54) HEART RATE ESTIMATION FROM FACE VIDEOS USING QUALITY BASED FUSION

(71) Applicant: Tata Consultancy Services Limited, Mumbai (IN)

(72) Inventors: Puneet Gupta, Kolkata (IN); Brojeshwar Bhowmick, Kolkata (IN); Arpan Pal, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 282 days.

(21) Appl. No.: 15/872,458

(22) Filed: Jan. 16, 2018

(65) Prior Publication Data

US 2018/0271390 A1    Sep. 27, 2018

(30) Foreign Application Priority Data

Mar. 21, 2017 (IN) .............................. 201721009872

(51) Int. Cl.
*A61B 5/024* (2006.01)
*A61B 5/00* (2006.01)
(Continued)

(52) U.S. Cl.
CPC ........ *A61B 5/02416* (2013.01); *A61B 5/0077* (2013.01); *A61B 5/1176* (2013.01);
(Continued)

(58) Field of Classification Search
CPC . A61B 5/02416; A61B 5/0077; A61B 5/1176; A61B 5/7221; G06K 9/00268; G06K 9/3233; G06T 7/0016
See application file for complete search history.

(56) References Cited

U.S. PATENT DOCUMENTS

| 8,360,986 B2 * | 1/2013 | Farag ................. A61B 5/02055 600/500 |
| 9,659,229 B2 | 5/2017 | Clifton et al. |

(Continued)

FOREIGN PATENT DOCUMENTS

EP        2960862        12/2015

OTHER PUBLICATIONS

Fernández, Alberto, et al. "Unobtrusive health monitoring system using video-based physiological information and activity measurements." 2015 International Conference on Computer, Information and Telecommunication Systems (CITS). IEEE, 2015. (Year: 2015).*

(Continued)

*Primary Examiner* — David J. McCrosky
*Assistant Examiner* — Chanel J Jhin
(74) *Attorney, Agent, or Firm* — Finnegan, Henderson, Farabor, Garrett & Dunner LLP

(57) ABSTRACT

A system and method for real time estimation of heart rate (HR) from one or more face videos acquired in non-invasive manner. The system receives face videos and obtains several blocks as ROI consisting of facial skin areas. Subsequently, the temporal fragments are extracted from the blocks and filtered to minimize the noise. In the next stage, several temporal fragments are extracted from the video. The several temporal fragments, corrupted by noise are determined using an image processing range filter and pruned for further processing. The HR of each temporal fragment, referred as local HR is estimated along with its quality. Eventually, a quality based fusion is applied to estimate a global HR corresponding to the received face videos. In addition, the disclosure herein is also applicable for frontal, profile and multiple faces and performs in real-time.

10 Claims, 2 Drawing Sheets

(51) Int. Cl.
  *G06T 7/00* (2017.01)
  *A61B 5/1171* (2016.01)
  *G06K 9/00* (2006.01)
  *G06K 9/32* (2006.01)
(52) U.S. Cl.
  CPC ........ *A61B 5/7221* (2013.01); *G06K 9/00268* (2013.01); *G06K 9/3233* (2013.01); *G06T 7/0016* (2013.01); *G06T 2207/30076* (2013.01); *G06T 2207/30201* (2013.01)

(56) References Cited

U.S. PATENT DOCUMENTS

| | | |
|---|---|---|
| 2013/0296660 A1 | 11/2013 | Tsien et al. |
| 2013/0324875 A1 | 12/2013 | Mestha et al. |
| 2014/0073861 A1* | 3/2014 | Rodriguez-Llorente ............. A61B 5/7246 600/301 |
| 2015/0282724 A1* | 10/2015 | McDuff ............ A61B 5/02427 600/479 |
| 2015/0302158 A1* | 10/2015 | Morris ............... A61B 5/02405 702/19 |
| 2016/0055635 A1* | 2/2016 | Yu ......................... G06T 7/0016 382/128 |
| 2017/0367590 A1* | 12/2017 | Sebe .................. G06K 9/00268 |
| 2018/0199838 A1* | 7/2018 | Lee ...................... A61B 5/1455 |

OTHER PUBLICATIONS

Zhang, Buyue, and Jan P. Allebach. "Adaptive bilateral filter for sharpness enhancement and noise removal." IEEE transactions on Image Processing 17.5 (2008): 664-678. (Year: 2008).*

Sellahewa, Harin, and Sabah A. Jassim. "Image-quality-based adaptive face recognition." IEEE Transactions on Instrumentation and measurement 59.4 (2010): 805-813. (Year: 2010).*

Bailey, "Range filters: local-intensity subrange filters and their properties," vol. , No. 3 (Year: 1985).*

Nandakumar, "Quality-based Score Level Fusion in Multibiometric Systems," ICPR (Year: 2006).*

* cited by examiner

HEART RATE ESTIMATION FROM FACE VIDEOS USING QUALITY BASED FUSION

PRIORITY CLAIM

This U.S. patent application claims priority under 35 U.S.C. § 119 to India Application No. 201721009872, filed on Mar. 21, 2017. The entire contents of the abovementioned application are incorporated herein by reference.

TECHNICAL FIELD

The embodiments herein generally relates to estimating heart rate and, more particularly, estimating heart rate using face videos acquired in a non-invasive manner and using quality based fusion.

BACKGROUND

The heart rate (HR) can be used to infer user physiological parameters associated with diseases like myocardial infarction, diabetic neuropathy, and myocardial dysfunction. Traditional electrocardiography (ECG) and photo-plethysmography (PPG) based HR estimation require human skin contact which is not only user uncomfortable, but also infeasible when multiple user monitoring is required or extreme sensitive conditions is a prime concern as in the case of monitoring: i) neonates; ii) sleeping human; and iii) skin damaged patients. These scenarios require non-invasive mechanism of HR measurement. It can be accomplished by estimating HR from face videos acquired using any camera like web-cams, smartphone camera or surveillance camera in a non-invasive manner.

Usually, existing face videos based HR estimation systems works in the following manner. Facial skin pixels are determined from the face video and referred as region of interest (ROI). Temporal signals depicting the motion or color variations in the frames across time, are estimated from the ROI using Eulerian or Lagrangian approaches. In a Lagrangian approach, temporal signals are determined by explicitly tracking the ROI or discriminating features over time. Such tracking is computationally expensive hence usually temporal signals are estimated using Eulerian approach, i.e., temporal signals are obtained by fixing ROI and analyzing its variations. The Eulerian approach works accurately for small variations. Noise in the temporal signals is filtered for accurate HR estimation. PPG is extracted from the filtered temporal signals and subsequently it is used to estimate the HR using R-R intervals or Fast Fourier Transform (FFT) spectrum. The confidence in the HR estimation known as quality, provides a useful indicator of the efficacy of estimated HR. In several quality measures have been proposed to evaluate the predicted HR in fitness monitoring environment. Existing systems do not use any quality parameter to improve the HR estimation, but rather to understand the effectiveness of the estimated HR.

In addition, along with the color motion variations, the camera also acquire several noises introduced by respiration, expression changes and eye blinking and environmental factors. Further, the variations in the different face parts vary according to the facial structure such as placement of arteries and bones in the face. HR estimation is a challenging problem due to these factors, especially when required in near real-time.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides a system and method for real time estimation of heart rate from one or more face videos acquired in non-invasive manner.

In one aspect, a method for real time estimation of heart rate from one or more face videos acquired in non-invasive manner. The method comprises one or more steps of receiving one or more face videos, obtaining one or more blocks consisting of facial skin areas of the received one or more face videos, extracting temporal fragments of the obtained one or more blocks of the one or more face videos, filtering the extracted temporal fragments using an image processing range filter and applying a predefined quality based fusion to estimate heart rate of the filtered temporal fragment of at least one face video of one or more face videos. The acquisition is based on the principle that there is a change in the blood flow when the heart beats. It introduces variations in the blood flow from heart to head through the carotid arteries that in turn results in the skin color change and head motion. In addition, the method employs the quality to improve the HR estimates.

In another aspect, a system for real time estimation of heart rate from one or more face videos acquired in non-invasive manner. The method comprises one or more steps of receiving one or more face videos, obtaining one or more blocks consisting of facial skin areas of the received one or more face videos, extracting temporal fragments of the obtained one or more blocks of the one or more face videos, filtering the extracted temporal fragments using an image processing range filter and applying a predefined quality based fusion to estimate heart rate of the filtered temporal fragment of at least one face video of one or more face videos. The acquisition is based on the principle that there is a change in the blood flow when the heart beats. It introduces variations in the blood flow from heart to head through the carotid arteries that in turn results in the skin color change and head motion. In addition, the system employs the quality to improve the HR estimates.

In another aspect, a non-transitory computer medium storing one or more instruction which when executed by a processor on a system, cause the processor to perform method for real time estimation of heart rate from one or more face videos acquired in non-invasive manner. The method comprises one or more steps of receiving one or more face videos, obtaining one or more blocks consisting of facial skin areas of the received one or more face videos, extracting temporal fragments of the obtained one or more blocks of the one or more face videos, filtering the extracted temporal fragments using an image processing range filter and applying a predefined quality based fusion to estimate heart rate of the filtered temporal fragment of at least one face video of one or more face videos. The acquisition is based on the principle that there is a change in the blood flow when the heart beats. It introduces variations in the blood flow from heart to head through the carotid arteries that in turn results in the skin color change and head motion. In addition, the system employs the quality to improve the HR estimates.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

BRIEF DESCRIPTION OF THE DRAWINGS

The embodiments herein will be better understood from the following detailed description with reference to the drawings, in which.

DETAILED DESCRIPTION OF EMBODIMENTS

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 1:
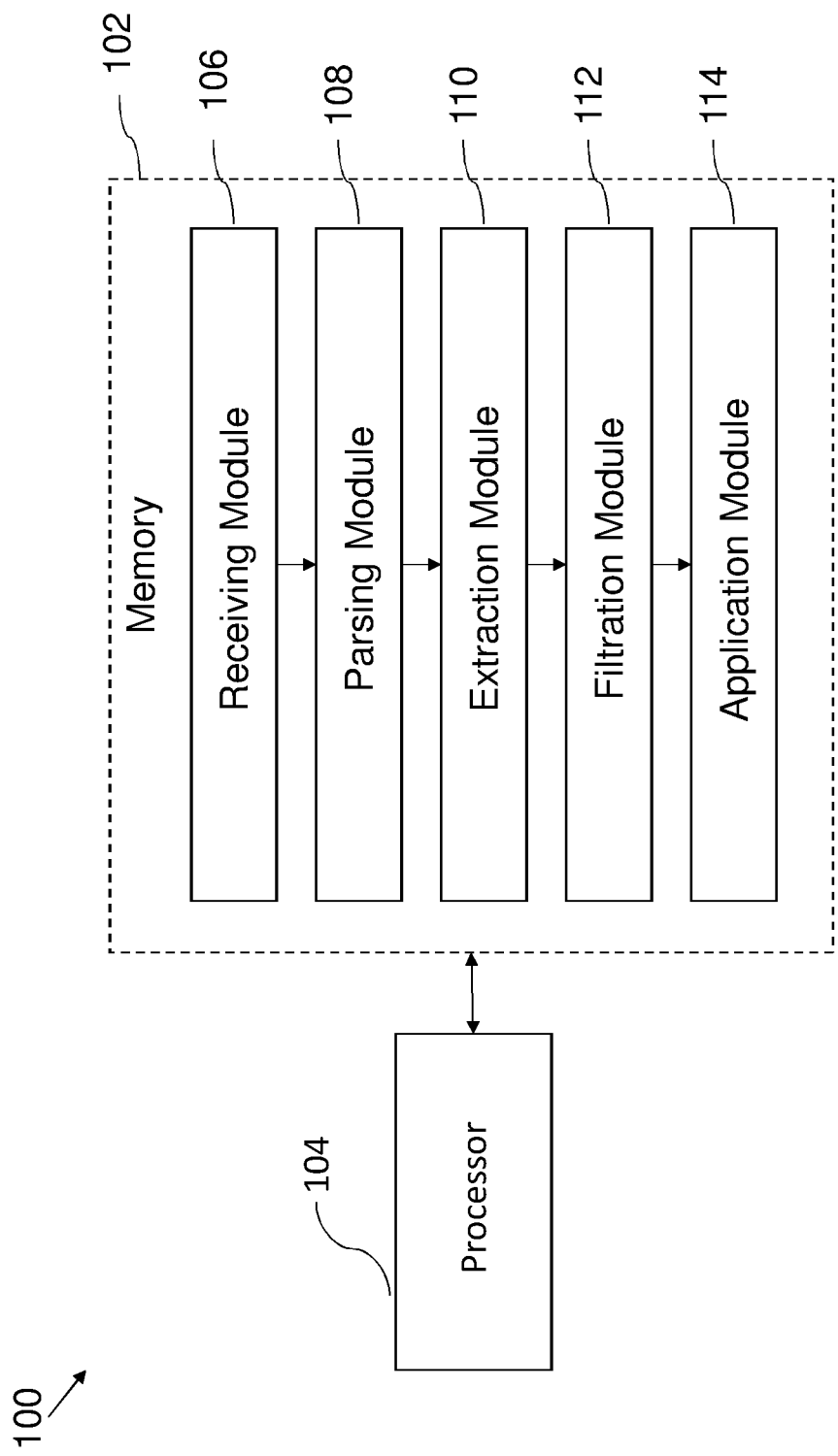
FIG. 1 illustrates a system for real time estimation of heart rate from one or more face videos acquired in non-invasive manner according to an embodiment of the present disclosure.

Referring FIG. 1, a system 100 for real time estimation of heart rate from one or more face videos acquired in non-invasive manner. The system comprises a memory 102, a processor 104 which is communicatively coupled with the memory, a receiving module 106, a parsing module 108, a extraction module 110, a filtration module 112, and an application module 114.

In the preferred embodiment, the receiving module 106 is configured to receive one or more face videos. It would be appreciated that the acquisition of videos are not limited to only face. It can acquire from any part of the human body but the acquisition must be in a non-invasive manner. The acquisition is based on the principle that there is a change in the blood flow when the heart beats. The heart beats introduces variations in the blood flow from heart to head through the carotid arteries that in turn results in change in skin color and head motion.

The rectangular face region is detected by applying Viola-Jones face detector on a frame of first video of the one or more face videos. Both frontal and profile face detectors are used for face detection. It would be appreciated that the model based face detection can also be used for better face detection.

In the preferred embodiment, the parsing module 108 is configured to obtain one or more blocks consisting of facial skin areas of the received one or more face videos. The one or more blocks of the one or more face videos are referred as region of interest (ROI).

In the preferred embodiment, the extraction module 110 is configured to extract temporal fragments of the obtained one or more blocks of the one or more face videos. Temporal fragments depicting the color or motion variations in the one or more blocks are estimated from the ROI. Each temporal fragment is sufficiently large to observe a peak due to noise rather than the variation introduced by HR.

It would be appreciated that among all the color channels, green channel contains the strongest plethysmographic fragments. Hence, the raw temporal fragment for a block is given by the mean green value of pixels inside it for each frame. The temporal fragment for a block i, Ti is:

$$T^i = [t_1^i, t_2^i, \ldots t_f^i] \quad (1)$$

where f is the total number of frames and tik represent the mean green value of ith block inside kth frame:

$$t_k^i = \frac{\Sigma_{(x,y) \in b_k^i} I_g(x, y)}{\Sigma_{(x,y) \in b_k^i} 1} \quad (2)$$

Such that bik denotes the ith block inside kth frame.

In the preferred embodiment, the filtration module 112 is configured to filter the extracted temporal fragments using an image processing range filter. Each extracted temporal fragment is composed of local PPG and that is corrupted by noise. The variations in different temporal fragments are different depending the facial structure, thus the temporal fragments are normalized using:

$$F_j^i = \frac{F_j^i - \mu(F_j^i)}{\sigma(F_j^i)} \quad (3)$$

where $F_j^i$ denotes the ith fragment in jth fragment while μ and σ represents the mean and variance operations respectively. The normalized fragment fragments can be written as:

$$F_j^i(n) = AP_a(n) + \eta(n) \quad (4)$$

Where Pa is the actual local PPG;
A is the channel matrix;
n is the time instant; and
η is the noise.

The local PPG is unknown and needs to be estimated from the fragment fragments. The estimated local PPG, Pe is given by:

$$P_e(n) = BF_j^i(n) TP_a(n) + \hat{\eta}(n) \quad (5)$$

where T is the transformation matrix while T=BA and $\hat{\eta}$=B η.

The PPG fragment contains one high frequency component corresponding to the HR pulse and small magnitude of other frequencies. Therefore, the estimated local PPG should possess high Kurtosis statistic which provides the shape information of the fragment both in terms of peakedness and tailness. The objective function required for local PPG extraction is:

$$\max_T |K[P_e]| \text{ subject to } T^*T = 1 \quad (6)$$

where ‖ and * denote the absolute value and the conjugate operations respectively while K [Pe] is the kurtosis for the samples in estimated PPG Pe.

In the preferred embodiment, the application module 114 is configured to apply a predefined quality based fusion to estimate heart rate of the filtered temporal fragment of at least one face video of one or more face videos. Each local HR estimate is weighed by its quality which indicates the confidence in accurate extraction of local HR from its local PPG.

$$q_j = \left(\frac{a_j - b_j}{b_j}\right) \quad (7)$$

where qj denotes the quality for local PPG signal, aj and bj denote the maximum and the second maximum amplitude of the frequency spectrum.

The local HR and their quality are fused using quality based fusion to estimate the global HR:

$$H_G = \frac{\sum_{j=1}^{p}(q_j \times h_j)}{\sum_{j=1}^{p} q_j} \quad (8)$$

where $H_G$ and p denote the global HR and total number of local HR estimates respectively.

Figure 2:
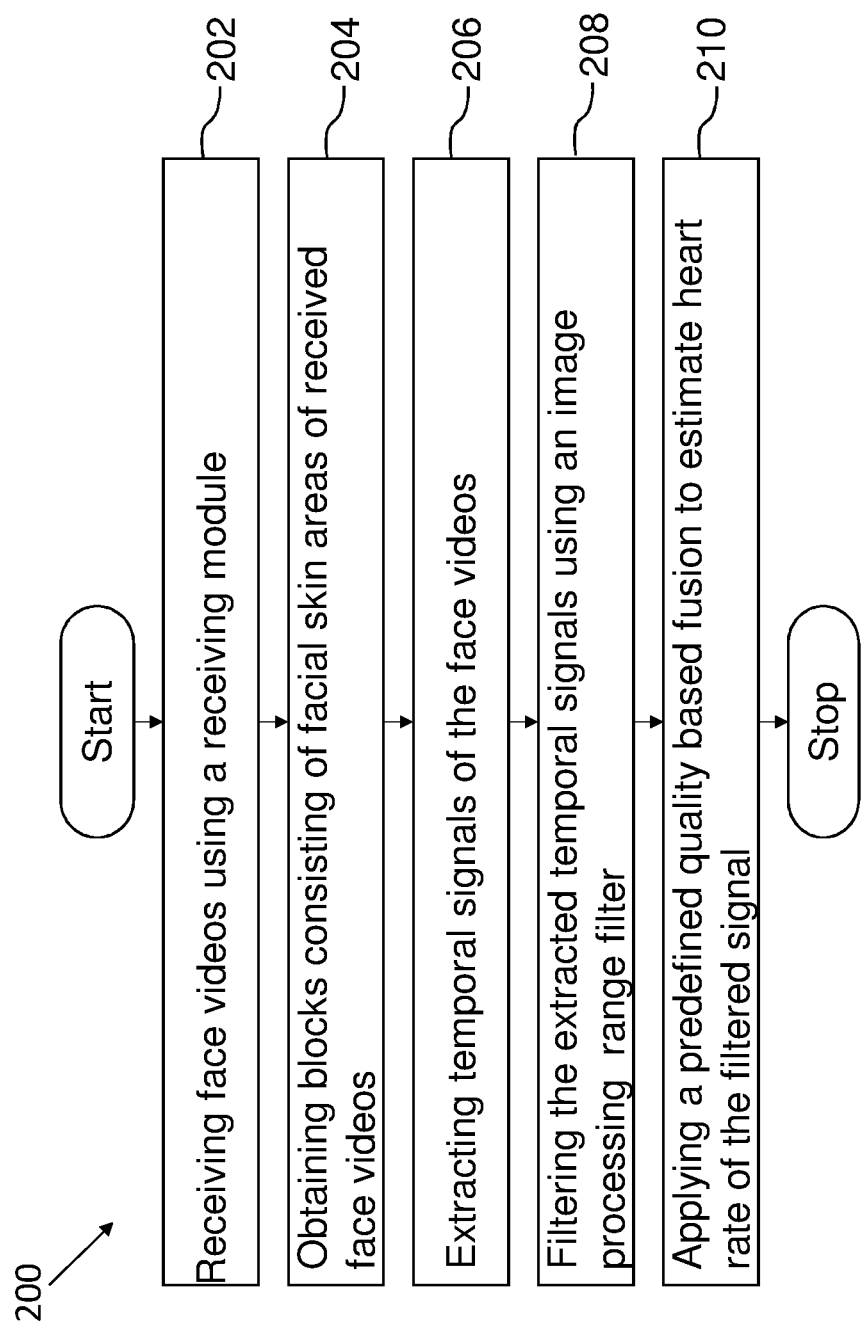
FIG. 2 illustrates a method for real time estimation of heart rate from one or more face videos acquired in non-invasive manner according to an embodiment of the present disclosure.

Referring FIG. 2, a method 200 for real time estimation of heart rate from one or more face videos acquired in non-invasive manner.

Initially, at the step 202, where the process receives one or more face videos, wherein each face video is divide into a plurality of temporal fragments. The acquisition is based on the principle that there is a change in the blood flow when the heart beats. The heart beats introduces variations in the blood flow from heart to head through the carotid arteries that in turn results in change in skin color and head motion.

At the step 204, where the process obtains one or more blocks consisting of facial skin areas of the received one or more face videos, wherein the one or more blocks are region of interest (ROI).

At the step 206, where the process extracts temporal fragments of the obtained one or more blocks of the one or more face videos. Each extracted temporal fragment of the plurality of temporal fragments is used to estimate a local heart rate. The extracted temporal fragment is composed of local PPG and that is corrupted by noise. The variations in different temporal fragments are different depending the facial structure and thus the temporal fragments are normalized with blind source separation methodology.

At the step 208, the process filters the extracted temporal fragments using an image processing range filter. The PPG fragment contains one high frequency component corresponding to the HR pulse and small magnitude of other frequencies. Therefore, the estimated local PPG should possess high Kurtosis statistic which provides the shape information of the fragment both in terms of peakedness and tailness.

Finally at the step 210, where the process applies a predefined quality based fusion to estimate heart rate of the filtered temporal fragment of at least one face video of one or more face videos. The local heart rate of each of the plurality of temporal fragments are consolidated to estimate global heart rate using quality based fusion.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein addresses problem that in a non-invasive and near real-time HR estimation along with the color and motion variations, the cameras acquire noise introduced by respiration, expression changes, camera parameters changes (for eg. focus), eye blinking and environmental factors. Further, the variations in the different face parts vary according to the facial structure, i.e., location of arteries and bones in the face. HR estimation is a challenging problem due to these factors, especially when required in near real-time.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A processor-implemented method for real time estimation of heart rate from one or more face videos acquired in a non-invasive manner, wherein the method comprising:
   receiving the one or more face videos, wherein the one or more face videos includes frontal and profile faces;
   obtaining one or more blocks consisting of facial skin areas of the received one or more face videos;
   extracting temporal fragments of the obtained one or more blocks of the one or more face videos, wherein the extracted temporal fragments comprising variants depending on facial structure;
   filtering the extracted temporal fragments using an image processing range filter, wherein the extracted temporal fragments of the one or more face videos comprising Photo-Plethysmography (PPG) are normalized using a local PPG, wherein the normalized temporal fragments is represented as $F_j^i(n)=AP_a(n)+\eta(n)$, where $F_j^i(n)$ is the $i^{th}$ normalized temporal fragment in $j^{th}$ fragment, $P_a$ is the local PPG, A is a channel matrix, n is time instant and $\eta$ is noise, wherein the local PPG having high Kurtosis statistic providing shape information with respect to peakedness and tailness of the extracted temporal fragments, and wherein the extracted temporal fragments are used to estimate a local heart rate from the local PPG; and
   applying a predefined quality based fusion to estimate the heart rate of the filtered temporal fragment of at least one face video of the one or more face videos, wherein the local heart rate of the extracted temporal fragments are consolidated to estimate the heart rate using the quality based fusion.

2. The method claimed in claim 1, wherein the one or more blocks are region of interest.

3. The method claimed in claim 1, wherein each face video is divided into a plurality of temporal fragments.

4. The method claimed in claim 1, wherein the estimated heart rate is a global heart rate.

5. A system for real time estimation of heart rate from one or more face videos acquired in a non-invasive manner, wherein the system comprising:
   a memory;
   a processor communicatively coupled with the memory, wherein the processor is configured to:
   receive the one or more face videos;
   obtain one or more blocks consisting of facial skin areas of the received one or more face videos;
   extract temporal fragments of the obtained one or more blocks of the one or more face videos, wherein the extracted temporal fragments comprising variants depending on facial structure;
   filter the extracted temporal fragments using an image processing range filter, wherein the extracted temporal fragments of the one or more face videos comprising Photo-Plethysmography (PPG) is normalized using a local PPG, wherein the normalized temporal fragments is represented as $F_j^i(n)=AP_a(n)+\eta(n)$, where $F_j^i(n)$ is the $i^{th}$ normalized temporal fragment in $j^{th}$ fragment, $P_a$ is the local PPG, A is a channel matrix, n is time instant and $\eta$ is noise, wherein the local PPG having high Kurtosis statistic providing shape information with respect to peakedness and tailness of the extracted temporal fragments, and wherein the extracted temporal fragments are used to estimate a local heart rate from the local PPG; and
   apply a predefined quality based fusion to estimate the heart rate of the filtered temporal fragment of at least one face video of the one or more face videos, wherein the local heart rate of the extracted temporal fragments are consolidated to estimate the heart rate using the quality based fusion.

6. The system claimed in claim 5, wherein the one or more face videos comprising of frontal and profile faces.

7. The system claimed in claim 5, wherein the one or more blocks are region of interest.

8. The system claimed in claim 5, wherein each face video is divided into a plurality of temporal fragments.

9. The system claimed in claim 5, wherein the estimated heart rate is a global heart rate using quality based fusion.

10. A non-transitory computer medium storing one or more instruction which when executed by a processor on a system, cause the processor to perform method for real time estimation of heart rate from one or more face videos acquired in a non-invasive manner comprising:
    receiving the one or more face videos, wherein the one or more face videos includes frontal and profile faces;
    obtaining one or more blocks consisting of facial skin areas of the received one or more face videos;
    extracting temporal fragments of the obtained one or more blocks of the one or more face videos, wherein the extracted temporal fragments comprising variants depending on facial structure;
    filtering the extracted temporal fragments using an image processing range filter, wherein the extracted temporal fragments of the one or more face videos comprising Photo-Plethysmography (PPG) is normalized using a local PPG, wherein the normalized temporal fragments is represented as $F_j^i(n)=AP_a(n)+\eta(n)$, where $F_j^i(n)$ is the $i^{th}$ normalized temporal fragment in $j^{th}$ fragment, $P_a$ is the local PPG, A is a channel matrix, n is time instant and $\eta$ is noise, wherein the local PPG having high Kurtosis statistic providing shape information with respect to peakedness and tailness of the extracted temporal fragments, and wherein the extracted temporal fragments are used to estimate a local heart rate from the local PPG; and applying a predefined quality based fusion to estimate the heart rate of the filtered temporal fragment of at least one face video of the one or more face videos, wherein the local heart rate of the extracted temporal fragments are consolidated to estimate the heart rate using the quality based fusion.

* * * * *